United States Patent
Suzuki et al.

(10) Patent No.: US 6,531,462 B2
(45) Date of Patent: *Mar. 11, 2003

(54) MEDICAMENT FOR TREATING OBESITY AND IMPROVING LIPID METABOLISM

(75) Inventors: Kunio Suzuki, 1238-8, Gomigaya, Tsurugashima-shi, Saitama 350-2202 (JP); Takeshi Shimizu, Saitama (JP); Tadashi Nakata, Saitama (JP)

(73) Assignees: Riken, Saitama (JP); Kunio Suzuki, Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/036,474

(22) Filed: Jan. 7, 2002

(65) Prior Publication Data

US 2002/0086855 A1 Jul. 4, 2002

Related U.S. Application Data

(60) Division of application No. 09/480,892, filed on Jan. 11, 2000, which is a continuation-in-part of application No. 09/186,158, filed on Nov. 5, 1998, now Pat. No. 6,046,184.

(30) Foreign Application Priority Data

Nov. 6, 1997 (JP) ................................. 9-304049
Aug. 25, 1998 (JP) ............................. 10-238144

(51) Int. Cl.$^7$ .............................................. A61K 31/56
(52) U.S. Cl. ......................................................... 514/177
(58) Field of Search ........................................ 514/177

(56) References Cited

U.S. PATENT DOCUMENTS

| 4,477,445 A | 10/1984 | Philibert et al. |
| 4,540,686 A | 9/1985 | Philibert et al. |
| 5,112,815 A | 5/1992 | Ambrus et al. |
| 5,264,428 A | 11/1993 | Streber |
| 5,420,121 A | 5/1995 | Suzuki |
| 5,610,152 A | 3/1997 | Suzuki |
| 5,710,143 A | 1/1998 | Suzuki et al. |
| 5,846,962 A | 12/1998 | Suzuki et al. |
| 6,046,184 A | * 4/2000 | Suzuki et al. |

FOREIGN PATENT DOCUMENTS

| EP | 442350 | 8/1991 |
| EP | 562849 | 9/1993 |
| EP | 617962 | 10/1994 |
| EP | 754457 | 1/1997 |
| JP | 2-275895 | 11/1990 |
| JP | 5-170651 | 7/1993 |
| JP | 7109216 | 4/1995 |
| JP | 7-165587 | 6/1995 |
| WO | 90/13559 | 11/1990 |
| WO | 98/57545 | 12/1998 |

OTHER PUBLICATIONS

Suzuki et al., Bioorg. Med. Chem. Lett., 8(16), 2133–2138 (1998).
Chemical Abstracts, vol. 123, No. 4, Abstract No. 40740, Columbus, Ohio, Jul. 1995.
Chemical Abstracts, vol. 109, No. 18, Abstract No. 156253, Columbus, Ohio, Oct. 1988.
Jamaluddin et al. Food Chemistry, vol. 54, No. 1, 9–13 (1995).
The Merck Index, Merck & Co., Whitehouse Station, "beta–sitosterol", p. 1467 (1996).

(List continued on next page.)

*Primary Examiner*—Sreeni Padmanabhan
*Assistant Examiner*—San-ming Hui
(74) *Attorney, Agent, or Firm*—Greenblum &Bernstein, P.L.C.

(57) ABSTRACT

A medicament for preventive and therapeutic treatment of obesity and a disease with abnormal lipid metabolism which comprises a 24-alkylcholest-5-en-3-one as an active ingredient.

10 Claims, 4 Drawing Sheets

OTHER PUBLICATIONS

Nair et al., Phytochemistry, vol. 12, No. 4, 903–906 (1973).
Parish et al., Synthelic Communications, 22(19), 2839–2847 (1992).
Cheng et al., Synthesis, 223–224 (1980).
Kasama et al. Journal of Chromatography, 400, 241–246 (1987).
CA 115:142347, Streber.
Suzuki et al., Bioorg, Med. Chem. Lett., 8(16), 2133–2138 (1998).
Cambie et al., Phytochemistry, vol. 30, No. 1, pp. 287–292, 1991.
Iritani et al., Lipids 1980; 15(5):371–4.
Daly, J. Agric. Food. Chem. 1983;31: 46–50.
Ponder et al., Abstract of Pediatr Res. 1992,32(6): 683–688.
Jenkins et al., J. Dairy Sci. 1986;69: 447–459.
English Abstract of Japanese Patent JP7109216 (1995).

* cited by examiner

MEDICAMENT FOR TREATING OBESITY AND IMPROVING LIPID METABOLISM

CROSS-REFERENCE TO RELATED APPLICATIONS

This application is a divisional of application Ser. No. 09/480,892, filed Jan. 11, 2000, which is a continuation-in-part of application Ser. No. 09/186,158, filed Nov. 5, 1998 now U.S. Pat. No. 6,046,184. The entire disclosures of application Ser. Nos. 09/480,892 and 09/186,158 are expressly incorporated by reference herein in their entireties.

BACKGROUND OF THE INVENTION

1. Field of the Invention

The present invention relates to medicaments useful for preventive and/or therapeutic treatment of obesity, and to medicaments of improving lipid metabolism.

2. Related Art

Obesity is caused by insufficient exercise of habitual hyperphagia, or by metabolic disturbance due to genetic causes or endocrine diseases and other. Obesity may be a risk factor that causes various adult diseases such as myocardial infarct or arterial sclerosis, and it may also be a cause for deteriorating these diseases. Therefore, early therapeutic and preventive treatment of obesity is very important. Diet therapies or exercise therapies have been applied heretofore as the treatment of mild obesity, and drug therapies are sometimes used for serious obesity in combination with these therapies.

Hormone drugs, metabolic accelerators and other have been used heretofore for drug therapies of obesity and lipid metabolic disorder. For example, androgens such as dehydroepiandrosterone and 3-keto-$\Delta^9$-19-norsteroid are known to have anti-obesity action (Japanese Patent Unexamined Publication No. (Hei)2-275895/1990). These androgens are considered to activate intramuscular anabolism to induce the consumption of depot lipid. It is also known that 3-ketosteroids such as 4-cholesten-3-one (Japanese Patent Unexamined Publication No. (Hei)5-170651/1993) and 5-cholesten-3-one (Japanese Patent Unexamined Publication No. (Hei)7-165587/1995) have reducing activity on serum lipid and anti-obesity action. However, the aformentioned cholestenones, which have the enone structure derived from cholesterol, may possibly be absorbed and accumulated in the body, and therefore, they are not satisfactory medicaments from a viewpoint of safety.

The object of the present invention is to provide a medicament for the treatment of obesity and a medicament for improving lipid metabolism. More specifically, the object of the present invention is to provide a highly safe medicament for the treatment of obesity and a medicament for improving lipid metabolism which are not absorbed and accumulated in the body.

SUMMARY OF THE INVENTION

The inventors of the present invention conducted various studies to achieve the foregoing object, and as a result, they found that 24-alkylcholestenones and their analogues deriving from plant sterols (24-alkylcholesterols) have extremely potent decreasing effect on serum lipid and body fat, and are useful as an active ingredient of a medicament for the treatment of obesity and a medicament for improving lipid metabolism. They also found that these substances exhibit the desired physiological activities without being substantially absorbed in the body. The present invention was achieved on the basis of these findings.

The present invention thus provides a medicament includinding a compound selected from the group consisting of 24-alkylcholestan-3-ones and 24-alkylcholesten-3-ones as an active ingredient a compound. According to preferred embodiments of the present invention, there are provided the aforementioned medicament wherein the compound is selected from the group consisting of 24-alkylcholestan-3-ones, 24-alkylcholestmonoen-3-ones, 24-alkylcholestdien-3-ones, 24-alkylcholesttrien-3-ones and 24-alkylcholesttetraen-3-ones; the aforementioned medicament wherein the compound is represented by the following general formula (I):

wherein $R^1$ represents a lower alkyl group; $R^2$ represents hydrogen atom, a halogen atom, hydroxy group, or oxo group; and said compound may have 1 to 4 double bonds at 1, 4, 5, 6, 7, 8, 8(14), 9(11), 11, 14, 15, 16, 22, 23, 24, 25 and/or 25(27)-position(s).

According to further preferred embodiments of the present invention, there is provided a medicament comprising 24-alkylcholest-5-en-3-one. Preferred examples of the 24-alkylcholest-5-en-3-one include 5-sitosten-3-one (24-ethylcholest-5-en-3-one), 5-campesten-3-one (24-methylcholest-5-en-3-one) and a mixture thereof, and the most preferred example includes 5-campesten-3-one.

These medicaments may be used for preventive and/or therapeutic treatment of obesity of mammals including humans, or for preventive and/or therapeutic treatment of diseases with abnormal lipid metabolism, for example, hyperlipidemia. The medicaments can also be used as an inhibitor of lipid absorption or an agent for decreasing serum lipid.

According to further aspects of the present invention, there are provided a method for preventive and/or therapeutic treatment of obesity, or a method for preventive and/or therapeutic treatment of diseases with abnormal lipid metabolism, which comprises the step of administering an effective amount of the aforementioned compound to a mammal including human; and a use of the aforementioned compounds for the manufacture of the aforementioned medicaments. According to still further aspects of the present invention, a health food and a health beverage containing the aforementioned compounds; a feed for livestock and a feed for a fish containing the aforementioned compounds; the aforementioned feed for livestock and the feed for a fish used for improving the quality of flesh; a pet food containing the aforementioned compounds; and use of the aforementioned compounds for the manufacture of the aforementioned food, feed, or pet food.

PREFERRED EMBODIMENTS OF THE INVENTION

The active ingredient of the medicament of the present invention is selected from the group consisting of 24-alkylcholestan-3-ones and 24-alkylcholesten-3-ones. Although the number of double bonds contained in the 24-alkylcholesten-3-ones is not particularly limited, 1 to 4 double bonds may be preferred. Preferred compounds are selected from the group consisting of 24-alkylcholestmonoen-3-ones, 24-alkylcholestdien-3-ones, 24-alkylcholesttrien-3-ones, and 24-alkylcholesttetraen-3-ones. More preferred compounds may contain 1 to 3, more preferably 1 or 2 double bonds at an arbitrary position or positions. The number of double bonds present in the rings may preferably be 1 to 3, more preferably 1 or 2, and they may be conjugated when two or more double bonds are present.

More specifically, 24-alkylcholest-4-en-3-ones, 24-alkylcholest-5-en-3-ones, 24-alkylcholest-6-en-3-ones, 24-alkylcholest-7-en-3-ones, 24-alkylcholest-8-en-3-ones, 24-alkylcholest-8(14)-en-3-ones, 24-alkylcholest-9(11)-en-3-ones, 24-alkylcholest-14-en-3-ones, 24-alkylcholest-4,6-dien-3-ones, 24-alkylcholest-5,7-dien-3-ones, 24-alkylcholest-5,8-dien-3-ones, 24-alkylcholest-5,9(11)-dien-3-ones, 24-alkylcholest-8,14-dien-3-ones, 24-alkylcholest-1,4,6-trien-3-ones, 24-alkylcholest-4,22-dien-3-ones, 24-alkylcholest-5,22-dien-3-ones, 24-alkylcholest-7,22-dien-3-ones, 24-alkylcholest-8,22-dien-3-ones, 24-alkylcholest-8(14),22-dien-3-ones, 24-alkylcholest-9(11),22-dien-3-ones, 24-alkylcholest-14,22-dien-3-ones, 24-alkylcholest-4,6,22-trien-3-ones, 24-alkylcholest-5,7,22-trien-3-ones, 24-alkylcholest-5,8,22-trien-3-ones, 24-alkylcholest-5,9(11),22-trien-3-ones, 24-alkylcholest-8,14,22-trien-3-ones, 24-alkylcholest-1,4,6,22-tetraen-3-ones, 24-alkylcholest-5,25(27)-dien-3-ones, 24-alkylcholest-7,16,25-trien-3-ones, 24-alkylcholest-8,24-dien-3-ones, 24-alkylcholest-9(11),24-dien-3-ones, 5β-24-alkylcholestan-3-ones and the like may be used.

The compounds of the aforementioned formula (I) may be used as further preferred compounds. In the formula (I), $R^1$ represents a lower alkyl group. As the lower alkyl group, for example, a straight or branched chain alkyl having 1 to 4, preferably 1 to 3 carbon atoms may be used. For example, methyl group, ethyl group, n-propyl group, isopropyl group and other may be used. Among them, methyl group or ethyl group is preferred, and methyl group is most preferred. $R^2$ represents hydrogen atom, a halogen atom, hydroxy group, or oxo group (=O). As the halogen atom, any of fluorine atom, chlorine atom, bromine atom and iodine atom may be used. Bromine atom may preferably be used.

In the above formula (I), 1 to 4 double bonds may be present at a position or positions of 1, 4, 5, 6, 7, 8, 8(14), 9(11), 11, 14, 15, 16, 22, 23, 24, 25 and/or 25(27). However, it is readily apparent to those skilled in the art that double bonds are not present at adjacent positions. For example, when a double bond is present between the carbon atoms of 5- and 6-positions, a double bond cannot be present between 4- and 5-positions or between 6- and 7-positions. Among them, where the bond between 5- and 6-positions is a double bond may be preferred. Where the bond between 5- and 6-positions is a double bond and the other bonds are single bonds may be more preferred, and where the bond between 5- and 6-position is double bond, $R^2$ is hydrogen atom, and the other bonds are single bonds may further be preferred. Where $R^1$ is ethyl group, $R^2$ is hydrogen atom, the bond between 5- and 6-positions is double bond, and the other bonds are single bonds is most preferred.

Asymmetric carbon atoms are present in the 24-alkylcholestan-3-ones and 24-alkylcholesten-3-ones. Configurations of the asymmetric carbon atoms are not particularly limited, and they may be in either of S- or R-configuration (occasionally referred to as α- or β-position). As to the carbon atoms in the formula (I) whose configuration is explicitly shown, it is preferred that each of them is in the indicated configuration.

Examples of preferred active ingredient of the medicament of the present invention include 5-sitosten-3-one (24-ethylcholest-5-en-3-one), 5-campesten-3-one (24-methylcholest-5-en-3-one), and a mixture thereof, and an example of the most preferred active ingredient of the medicament of the present invention includes 5-campesten-3-one. Structures of the preferred active ingredients are shown below. However, the active ingredients of the medicament of the present invention are not limited to these compounds.

5-sitosten-3-one 5-campesten-3-one

24-Alkylcholestan-3-ones and 24-alkylcholesten-3-ones can be readily prepared by those skilled in the art basically according to known methods for preparing cholestan-3-one, cholesten-3-one and other. For example, the preparation of 5-sitosten-3-one, a typical compound that falls within the compounds represented by the formula (I), is specifically explained in the literature by Parish (Parish, E. J., et al, Synthetic Communications, 22(19), pp.2839–2847, 1992), or the compound can also be readily prepared by the method of Cheng (Cheng, Y. S., et al., Synthesis 1980, 223) by using β-sitosterol as a starting material. Accordingly, it can be readily understood by those skilled in the art that 24-alkylcholestan-3-ones and 24-alkylcholesten-3-ones can be prepared according to the methods described in the publications, or by referring to these methods and suitably modifying or altering the reaction conditions and/or reagents applied in the methods, if required. However, methods for preparing 24-alkylcholestan-3-ones and 24alkylcholesten-3-ones, preferably the compounds represented by the formula (I), are not limited to chemical synthetic method, and they can be prepared by biological means, e.g., culturing microorganisms or other, or alternatively, by using enzymes deriving from microorganisms.

The medicament of the present invention is characterized to comprise one or more compounds selected from the group consisting of 24-alkylcholestan-3-ones and 24-alkylcholesten-3-ones, and the medicament can be used for preventive and/or therapeutic treatment of obesity, and preventive and/or therapeutic treatment of diseases with abnormal lipid metabolism. Although it is not intended to be bound by any specific theory, the mode of action of the medicament of the present invention is considered to be a sense of inhibition against lipid absorption, which suppresses the formation of chylomicrons that act as lipid transport lipoproteins and are formed in mucous membrane cells of small intestine. It is considered that lipids released from body fat may compensate the shortage of lipid and consumed, which results in the decrease of weight gain. It is also presumed that lipids, deriving from food or feed, that are untransported into the body and remain in mucous membrane cells of small intestine are excreted into intestinal lumen together with the cells during the fast reintegration of the cells. However, the scope of the present invention is not limited by the aforementioned mode of action.

Types of obesity to which the medicament of the present invention can be applied are not particularly limited by their causes. For example, the medicament of the present invention may be applied to any types of obesity such as those caused by the lack of exercise or overeating, by genetic disorder, by the disorder of regulatory mechanism of appetite, by metabolic disturbance due to endocrine diseases, by mental disorder or other. Examples of the diseases with abnormal lipid metabolism include, for example, hyperlipidemia and fatty liver caused by abnormal lipid metabolism, and examples also include arterial sclerosis, hypertension, diabetes, gout and other. The medicament of the present invention can also be used as an inhibitor of lipid absorption or an agent for decreasing serum lipid. The medicament of the present invention can be applied to mammals including human.

As the medicament of the present invention, a compound selected from the group consisting of 24-alkylcholestan-3-ones and 24-alkylcholesten-3-ones, per se, may be used. However, it is generally preferred to use a pharmaceutical composition which is prepared by using pharmaceutically acceptable additives. The medicament of the present invention can be administered orally or parenterally. Examples of the pharmaceutical compositions suitable for oral administrations include, for example, tablets, granules, capsules, powders, liquids, syrups and other. Examples of the pharmaceutical compositions suitable for parenteral administrations include, for example, injections, drip infusions, suppositories, transdermal preparations and other. However, dosage forms of the medicament of the present invention are not limited to these examples. Doses of the medicament of the present invention should be appropriately increased or decreased depending on the age, conditions and other of a patient, the route of administration and other factors. Generally, the dose may be within the range of 1 to 5,000 mg per day for an adult.

Pharmaceutical additives used for the preparation of the medicament of the present invention are not particularly limited, and they can be suitably chosen by those skilled in the art. For example, excipients, binders, lubricants, dispersing agents, suspending agents, emulsifiers, buffering agents, antioxidants, antiseptics, isotonic agents, pH modifiers, solubilizing agents, stabilizers and other can be used. Substances used for each of the aforementioned purposes are well known to those skilled in the art. The active ingredient of the medicament of the present invention, i.e., a compound selected from the group consisting of 24-alkylcholestan-3-ones and 24-alkylcholesten-3-ones, is lipophilic. Therefore, the active ingredient can be dissolved in an oily substance and applied as oral administration, for example, dissolved in natural edible oils such as sesame oil, soybean oil, corn oil, olive oil, cotton seed oil, middle chain fatty acid triglycerides such as Panacete and other. In that case, an oily solution containing the active ingredient may preferably be encapsulated in capsules, and applied as oral administration. Such means are well known to those skilled in the art and ordinarily used.

The health food and the health beverage containing a compound selected from the group consisting of 24-alkylcholestan-3-ones and 24-alkylcholesten-3-ones can be used for the purpose of health care, for example, to inhibit the accumulation of body fat and maintain appropriate body weight. Types of the health food and the health beverage are not particularly limited, and whose examples include processed food, seasonings, so-called drinks, refrigerants and other. One or more compounds selected from the group consisting of 24-alkylcholestan-3-ones and 24-alkylcholesten-3-ones can be added in the foods and beverages. Manufacturing processes thereof are also not particularly limited. Generaliy, processed foods can be prepared by adding beforehand a compound of the formula (I) in oils and fats used as raw materials of processed foods, or alternatively, by adding a compound of the formula (I) during processing procedures by suitable means. A compound selected from the group consisting of 24-alkylcholestan-3-ones and 24-alkylcholesten-3-ones may be added in an amount of 1 mg to 5,000 mg based on 100 g of a food or a beverages.

The feeds for livestock and the feeds for fishes which contain a compound selected from the group consisting of 24-alkylcholestan-3-ones and 24-alkylcholesten-3-ones can be used for the purpose of, for example, suppressing excess accumulation of body fat of livestock such as cattle and pigs and cultured fishes such as young yellowtail and a sea bream to improve the quality of flesh. The pet foods containing a compound selected from the group consisting of 24-alkylcholestan-3-ones and 24-alkylcholesten-3-ones can be used for the purpose of suppressing obesity and health care of pet animals (also called partner animals) such as dogs or cats. Forms of the feed and the pet food as well as manufacturing processes thereof are not particularly limited, and forms and processes can be appropriately chosen by those skilled in the art. Generally, desired feed or pet foods can be easily prepared by adding beforehand the aforementioned compound in oils and fats used as raw materials, or alternatively, by adding the above compound during processing procedures by suitable means. One or more compounds selected from the group consisting of 24-alkylcholestan-3-one and 24-alkylcholesten-3-one can be added in the feed and the pet food.

EXAMPLES

The present invention will be further explained more specifically by referring to the examples. However, the scope of the present invention is not limited to these examples.

Example 1

(A) Materials and Methods

5-Sitosten-3-one was prepared according to the method of Parish (Parish, E. J., et al., Synthetic Communication, 22, pp.2839–2847, 1992) by using β-sitosterol (Tokyo Chemical Industry Co., Ltd.) as a starting material and used in the experiments. The content ratio of 24-ethyl and 24-methyl compounds in the synthesized product was 6.5:3.5. As experimental animals, six CDF1 male mice (5-week old, Charles River Japan Inc.) were used in each experimental group. The animals were fed in aluminum cages for mice, and allowed to feed and water ad libitum. The animals were fed for 2 weeks under feeding conditions at a temperature of 24±1° C. and a relative humidity of 55±5%, where light and darkness were controlled to change every 12 hours, and each cage and floor mat (white flakes) were exchanged twice a week.

Modified AIN (Oriental Yeast Co.) was used as basic feed and mixed with 0.5% 5-sitosten-3-one to prepare test feeds. A feed used as a positive control was prepared by adding 0.5% of 4-cholesten-3-one (Japanese Patent Unexamined Publication No. Hei 5-170651/1993) to the basic feed. Non-treated mice as a control were fed solely with the basic feed. The basic feed was composed of 22.8% crude protein, 54.1% carbohydrates, 6.0% lipids, 4.9% fibers, 2.9% ash, and 8.7% water, and its calorie was 1,523 kJ. The feed was stored at 4° C. after preparation, and a fresh feed was supplied every day.

The animals were weighed at given intervals of time, and the average values and standard errors of the experimental groups were determined. In addition, feed consumptions were measured at given intervals of time and daily averages per mouse were determined. The animals were observed every day. After the end of the feeding, the animals were anesthetized to death with carbon dioxide gas, and bloods were collected from the vena cava to obtain serums. The animals were autopsied, and the brains, lungs, hearts, livers, spleens, kidneys, testis, adrenals and intraperitoneal fat were examined by the naked eye and weighed. As to serum lipid, neutral fats were measured by using a clinical test kit based on the enzyme method (Triglyceride-E Test, Wako Pure Chemicals Industries Co., Ltd.), and total cholesterol and cholestanol were measured by the method of Kasama (T. Kasama, et al., J. Chromatogr., 400, 241, 1987) with modifications, where the amount of benzoyl chloride was increased by 10 times, the reaction time was doubled, and the measurement was performed by using a high performance liquid chromatography system. Significant differences were determined by t-test for body weights and serum lipids on the basis of the the non-treated control mice.

(B) Test Results (1) Changes in Body Weight

Figure 1:
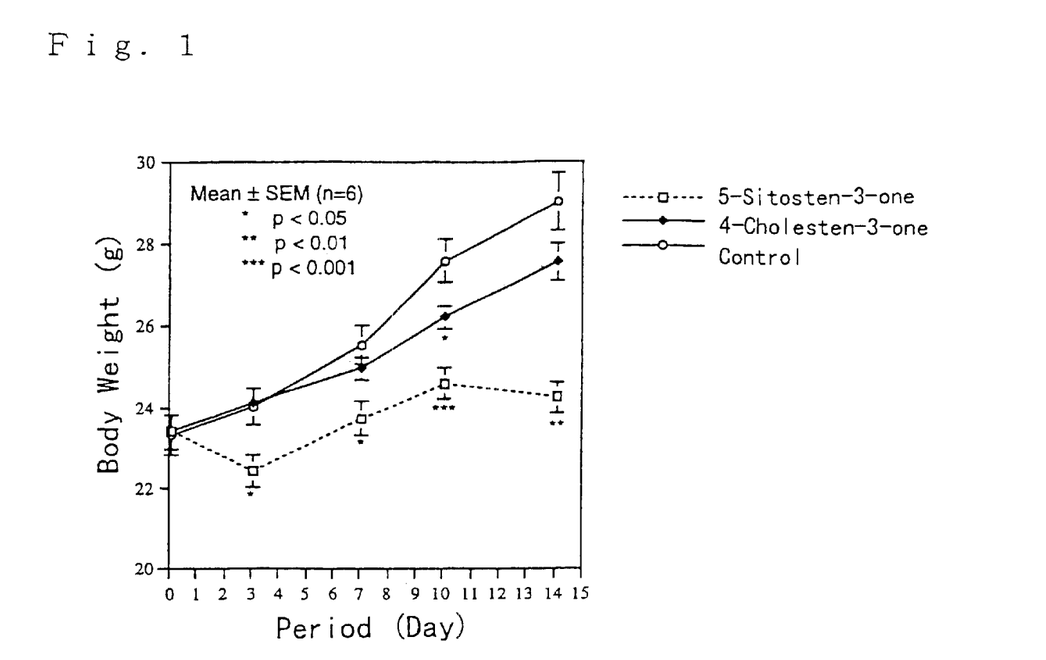
FIG. 1 depicts inhibitory effects on the weight gain of mice fed with a feed supplemented with 0.5% of 5-sitosten- 3-one or 4-cholesten-3-one as a positive control. In the figure, asterisks *,  and * show the presence of a significant decrease from the non-treated control mice at a probability (p) levels of 5% or less, 1% or less, and 0.1% or less, respectively, in a t-test.

The changes in body weight of the test animals are shown in FIG. 1. The increase in body weight was remarkably suppressed in the mice fed with the feed supplemented with 5-sitosten-3-one (0.5%) compared to the non-treated control mice. The inhibitory effect was markedly stronger than that observed in the positive control group treated with 4-cholesten-3-one. In the figure, asterisks *,  and * show the presence of a significant decrease from the non-treatel mice at probability (p) levels of 5% or less, 1% or less, and 0.1% or less, respectively, in a t-test.

(2) Changes in the Amount of Body Fat

Figure 2:
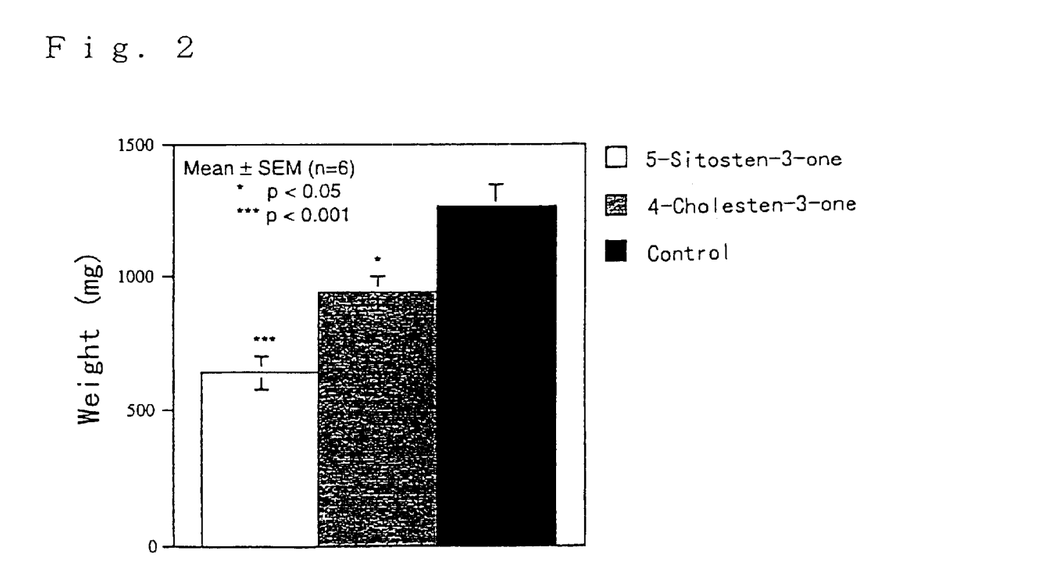
FIG. 2 depicts the decrease of body fat (intraperitoneal fat) of mice fed with a feed supplemented with 0.5% of 5-sitosten-3-one. In the figure, asterisks * and *** show the presence of a significant decrease from the non-treated control mice at a probability (p) levels of 5% or less and 0.1% or less, respectively, in a t-test.

Remarkable decreases of body fat (subcutaneous fat and intraperitoneal fat) were observed in the mice fed with the feed supplemented with 5-sitosten-3-one (0.5%) for two weeks. Degree of the decrease was greater than that observed in the positive control group treated with 4-cholesten-3-one, and the amount of intraperitoneal fat was the half of that observed in the non-treated control mice (FIG. 2). In the figure, asterisks * and *** show the presence of a significant decrease from the non-treated mice at probability levels (p) of 5% or less and 0.1% or less, respectively, in a t-test.

(3) General Conditions and Autopsical Finding

General conditions of the mice administered with 5-sitosten-3-one were normal in terms of good hair gloss and active behavior, except their thinner bodies as compared to the control mice, and no abnormality was observed in the eyes, mucosa, feces, behavior and other. The appetite was also normal except for slight suppression (Table 1). The autopsy after the end of the feeding revealed a slight weight decrease in kidneys of the mice treated with 5-sitosten-3-one; however, further investigations verified that the decrease was not from any toxic influence. No pathological abnormality was observed in the other organs and tissues. On the other hand, the enlargements of spleens were recognized in the positive control treated with 4-cholesten-3-one.

TABLE 1

| Test group | g/mouse/day |
|---|---|
| Control | 4.96 |
| 4-Cholesten-3-one | 4.80 |
| 5-Sitosten-3-one | 4.43 |

As to serum lipids of the 5-sitosten-3-one group, neutral fats and total cholesterol remarkably decreased down to 15% and 51%, respectively, as compared to the non-treated control mice (Table 2). The above decreasing effect on serum lipids was found to be most potent compared to 4-cholesten-3-one and other cholestenone derivatives (Tables 2 and 3).

In the 4-cholesten-3-one group as the positive control, cholestanol, a metabolite of the administered substance, was detected in serums. In the colesta-4,6-dien-3-one, 6β-bromo-4-cholesten-3-one, and 5β-cholestan-3-one groups, i.e., treated with cholestenone derivatives, cholestanol or coprostanol as a metabolite of the test compounds was detected in serums (Table 3). Since these metabolites can hardly be further metabolized, they may possibly accumulate in organs to cause disorders when their precursors are administered repeatedly. On the other hand, no cholestanol and other metabolites were detected in the group treated with 5-sitosten-3-one (Table 2).

5-Cholesten-3-one and 6β-bromo-4-cholesten-3-one as cholestenone derivatives showed potent appetite suppressing effects, although the appetite suppressing effect of 5-sitosten-3-one was weak (Tables 1 and 3). From these results, it was shown that the medicament of the present invention is a safe medicament with extremely low toxicity, and useful for therapeutic and/or preventive treatment of hyperlipidemia or obesity.

Example 2

(A) Materials and Methods

As 24-alkylcholesten-3-ones, (1) 4-sitosten-3-one, (2) 6α-hydroxy-4-sitosten-3-one, and (3) 6-hydroxy-4-sitosten-3-one (α:β=2.6:1) were synthesized by using β-sitosterol (Tokyo Chemical Industries Co., Ltd.). The content ratio of 24-ethyl and 24-methyl compounds in the synthesized product was 6.5:3.5. As experimental animals, six CDF1 male mice (5-week old, Charles River Japan Inc.) were used in each experimental group. A purified feed (Modified AIN, Oriental Yeast Co.) was used as a basic feed and mixed with 0.5% test compounds to prepare test feeds. The animals were allowed to feed and water ad libitum. The animals were weighed and observed to examine general conditions twice a week. The animals were subjected to autopsy after the end of the feeding, and their bloods were collected. Lipid concentrations in the separated serums were measured by using a clinical test kit based on the enzyme method (Wako Pure Chemicals Industries Co., Ltd.). Significances of the resulting experimental values were examined by the variance analysis. The other experimental conditions were the same as in Example 1.

(B) Experimental Results

Figure 3:
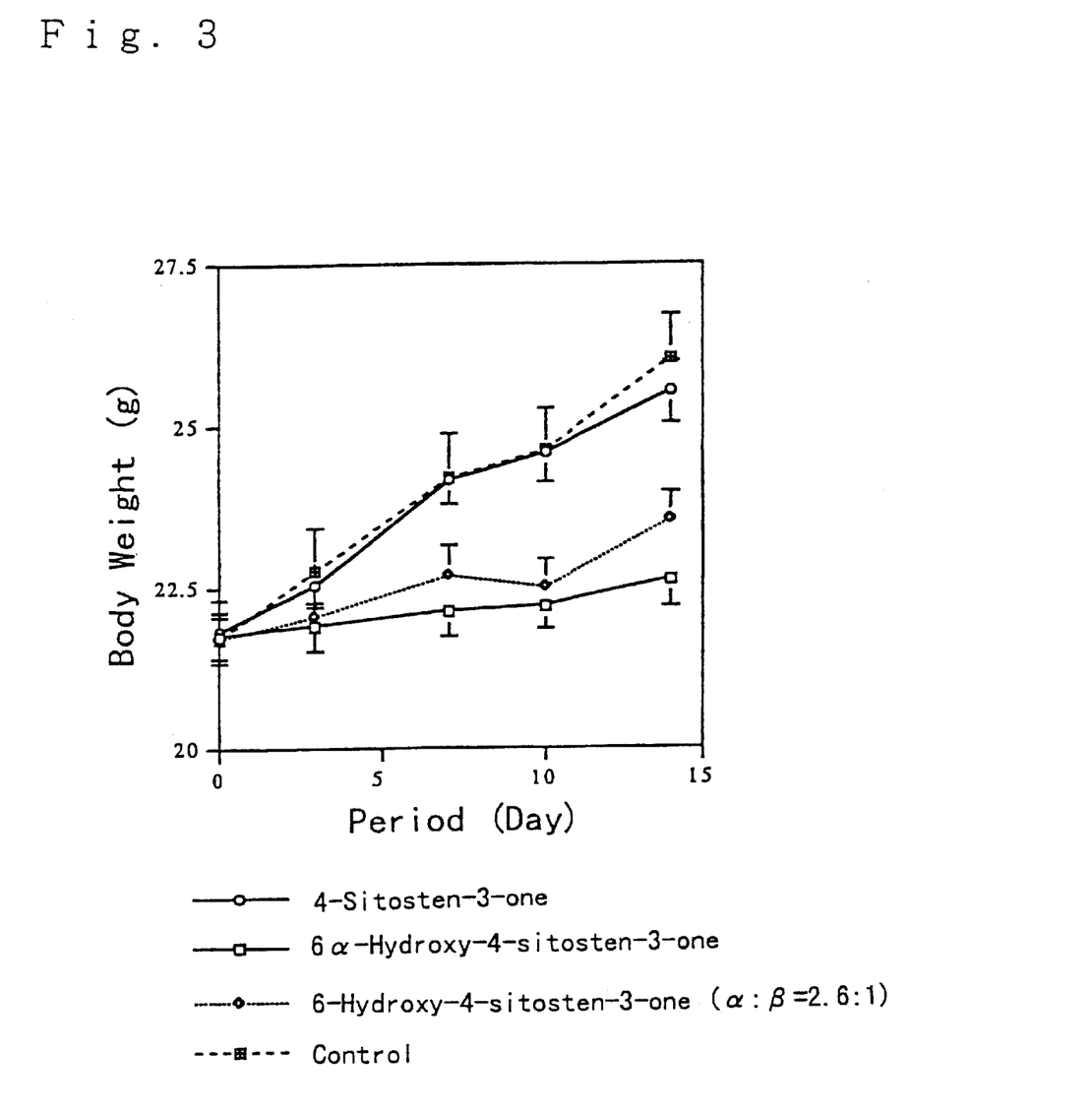
FIG. 3 depicts the results of inhibitory effects on the weight gain of mice fed with a feed supplemented with 0.5% of 4-sitosten-3-one, 6α-hydroxy-4-sitosten-3-one, or 6-hydroxy-4-sitosten-3-one (α:β=2.6:1), in comparison with that of the non-treated control mice. The values in the figure are indicated as mean±standard error.

4-Sitosten-3-one exhibited no significant suppression of body weight, whereas 6-hydroxy-4-sitosten-3-one showed potent suppressing effects on body weight in both of the group treated with α-compound and the group treated with the mixture of α- and β-isomers (2.6:1). In particular, in the α-compound group, almost equal to or more potent effects were observed compared to the 5-sitosten-3-one group (FIG. 3). Slight decrease of feed intake and remarkable decrease of feed efficiency were observed in the 6-hydroxy-4-sitosten-3-one group for both of the α-isomer and the mixture of α- and β-isomers, whereas only slight changes were observed in the 4-sitosten-3-one group (Table 4).

TABLE 2

Serum lipid of CDF1 mice administered with 5-sitosten-3-on

| | No. of Mice | Neutral fats | | Total cholesterol | | Cholestanol | |
|---|---|---|---|---|---|---|---|
| | | Mean ± standard error mg/dl | P | Mean ± standard error mg/dl | P | Mean ± standard error mg/dl | P |
| Control | 6 | 366.9 ± 12.3 | | 159.6 ± 5.4 | | 0 | |
| 4-Cholesten-3-one | 6 | 197.7 ± 28.1 | <0.001 | 99.2 ± 5.8 | <0.001 | 63.5 ± 3.7 | <0.001 |
| 5-Sitosten-3-one | 6 | 56.5 ± 8.2 | <0.001 | 81.3 ± 3.0 | <0.001 | 0 | |

TABLE 3

Comparison of effect of cholestenones and 5-sitosten-3-one on body weight gain, serum lipid and feed intake of CDF1 mice

| | Body weight gain | Intraperitoneal fat | Serum neutral fats | Serum cholesterol | Serum metabolite | Feed intake |
|---|---|---|---|---|---|---|
| 4-Cholesten-3-one | 72[a] | 74 | 54 | 62 | Cholestanol | 97 |
| 5-Cholesten-3-one | −16 | 37 | 30 | 68 | 0 | 61 |
| Colesta-4,6-dien-3-one | 59 | 69 | 60 | 63 | Cholestanol | 79 |
| 4-Cholestene-3,6-dione | −62 | 23 | 36 | 60 | 0 | 101 |
| 6-Hydroxy-4-cholesten-3-one | 50 | 63 | 47 | 80 | 0 | 96 |
| 6 β-Bromo-cholesten-3-one | 48 | 62 | 89 | 98 | Cholestanol | 71 |
| 5 β-Cholestan-3-one | 51 | 71 | 70 | 75 | Cholestanol | 91 |
| 5-Sitosten-3-one | 56 | 50 | 15 | 51 | 0 | 89 |

[a]Values in the table indicate ratios (%) relative to the non-treated control group.

TABLE 4

|  | Body weight gain (g/mouse) | Feed intake (g/mouse) | Feed efficiency* (body weight gain/feed intake) |
| --- | --- | --- | --- |
| 4-Sitosten-3-one | 3.71 | 42.78 | 0.087 |
| 6 α-Hydroxy-4-sitosten-3-one | 0.86 | 39.60 | 0.022 |
| 6-Hydroxy-4-sitosten-3-one (α:β = 2.6:1) | 1.82 | 41.77 | 0.044 |
| Control | 4.31 | 43.0 | 0.10 |

The numerical values are shown as the total values for 14 days.

As shown in Table 5, intraperitoneal fat was decreased by 60% and 50% in the 6α-hydroxy-4-sitosten-3-one and 6-hydroxy-4-sitosten-3-one groups, respectively. However, the decrease in the 4-sitosten-3-one group was not signilficant. These three compounds exhibited potent decreasing effects on triglyceride and free fatty acid in plasma, and their potencies were decreased in the order of 1>3≧2. Total cholesterol and phospholipid concentrations in plasma were also significantly decreased by 6α-hydroxy-4-sitosten-3-one and 6-hydroxy-4-sitosten-3-one. However, the effects were only slight and no change in HDL-cholesterol was observed. The asterisk * in the table show the presence of a significant decrease from the non-treated mice at probability (p) level of 5% or less in a variance analysis.

TABLE 5

|  | Control | 4-Sitosten-3-one | 6α-Hydroxy-4-sitosten-3-one | 6-Hydroxy-4-sitosten-3-one (α:β = 2.6:1) |
| --- | --- | --- | --- | --- |
| Intraperitoneal fat (mg) | 944.4 ± 88.5 | 841.5 ± 69.0 | 369.8 ± 22.5* | 481.8 ± 51.9* |
| Triglyceride (mg/dl) | 197.6 ± 15.2 | 130.9 ± 4.9* | 66.8 ± 3.5* | 76.5 ± 5.2* |
| Total cholesterol (mg/dl) | 164.4 ± 4.7 | 151.4 ± 5.7 | 142.5 ± 5.1* | 133.3 ± 5.7* |
| HDL-cholesterol (mg/dl) | 50.9 ± 15.0 | 42.4 ± 6.36 | 36.7 ± 4.7 | 45.0 ± 5.8 |
| Phospholipid (mg/dl) | 267.5 ± 10.1 | 271.0 ± 9.5 | 209.6 ± 7.8* | 211.9 ± 5.1* |
| Free fatty acid (mEq/dl) | 1.40 ± 0.09 | 0.92 ± 0.03* | 0.69 ± 0.04* | 0.77 ± 0.03* |

Values indicate mean (n = 6) ± standard error.
*Significant difference (p < 0.05)

Example 3
(A) Materials and Methods

5Sitosten-3-one was synthesized from β-sitosterol (Tokyo Chemical Industry Co., Ltd.) according to the method of Parish (Parish, E. J., et al., Synthetic Communication, 22, pp.2839–2847, 1992), and purified by silica gel column chromatography and recrystallization. The content ratio of 24-ethyl isomer and 24-methyl compounds in the synthesized product was 6.5:3.5. As experimental animals, thirty 4-week old CDF1 male mice were purchased from Charles River Japan Inc. and divided into five experimental groups each composed of six mice. The test compounds were administered as the admixture in feeds, and the following groups were provided: (1) 0.1% addition, (2) 0.3% addition, (3) 0.5% addition, (4) a lipid-free feed without the addition of the test compound, and (5) control group without the addition of the test compound. A purified feed (modified AIN, Oriental Yeast Co.) was used as a basic feed, and supplemented with 10% soybean oil (Wako Pure Chemical Industries Co., Ltd.) to prepare solid feeds with or without the addition of the test compound. The lipid-free feed, per se, was processed to obtain solid feed. The animals were fed for a week with the feed for the control without the addition of test compound for acclimatization, and then the animals were allowed to feed with the respective feed ad libitum.

Each group of animals was housed in an aluminum cages of 22×33×11(h)cm (6 mice per a cage), and feedings were carried out at a temperature of 24±1° C. and a relative humidity of 55±5%, where light and darkness were controlled change every 12 hours. Measurements of body weights and feed intakes, and observations of general conditions were conducted three times a week. After the feeding for 3 week with the test feeds, the animals were subjected to autopsy and their bloods were collected. As serum lipid analyses, triglyceride, phospholipid, free fatty acid, total cholesterol, and HDL-cholesterol were measured by using a clinical test kit (Wako Pure Chemicals Industries Co., Ltd. ). Significances of the resulting values were examined by the variance analysis for the groups treated with the medicament, or by the t-test for the lipid-free feed group.

(B) Test Results
(1) Changes in Body Weight

Figure 4:
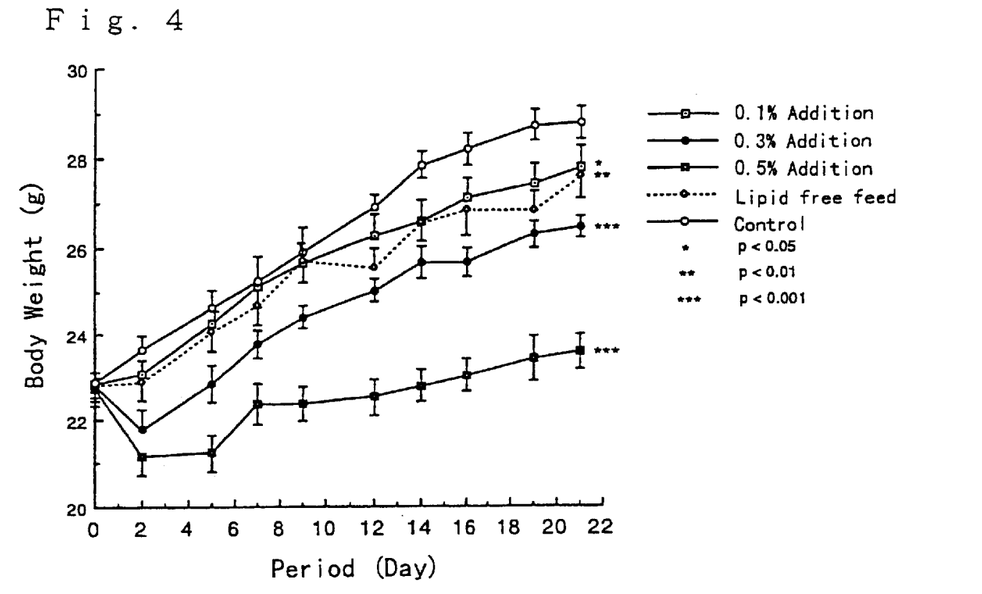
FIG. 4 depicts the dose response of 5-sitosten-3-one to the inhibitory effect on the weight gain of mice fed with a feed supplemented with 5-sitosten-3-one, in comparison with the non-treated control group and mice fed with a lipid-free feed. The values in this figure are indicated as mean±standard error. Asterisks *,  and * show the presence of a significant decrease from the non-treated control mice at a probability (p) of 5% or less, 1% or less, and 0.1% or less, respectively, in a variance analysis.

As shown in FIG. 4, body weight decreases were observed in all of the mice treated with 5-sitosten-3-one, and dose-dependent effects were recognized in proportion to the added amounts of 0.1%, 0.3% and 0.5%. In the 0.3% and 0.5% groups, sharp decrease of body weight was observed due to the decrease of feed intake immediately after the start of the administration. The decrease of feed intake in these groups was recovered afterwards; however, body weight gains were slow and the differences from the control group were increased progressively. In particular, the body weight gains in the 0.5% addition group were small, and the body weights were kept substantially unchanged. Significant suppression of body weight gain was also observed in the lipid-free diet group, and the results from this group gave a similar experimental curve to that of the 0.1% addition group.

(2) Feed Intake and Feed Efficiency

Feed intake of the group treated with 0.1% 5-sitosten-3-one was unchanged, and that of the 0.3% addition group was slightly decreased. The 0.5% addition group exhibited about 13% decrease in total for 3 weeks. In contrast, the increase of feed intake was observed in the lipid-free feed group (Table 6). Feed efficiencies were decreased dose-dependently in groups treated with the medicament, and the 0.5% addition group gave particularly significant decrease, i.e., about 80% decrease compared to the control group. The lipid-free feed group gave the decrease by about 20%, which is similar to that of the 0.1% addition group. It is apparent from these results that the suppression of body weight gain by 5-sitosten-3-one is more closely related to the decrease of feed efficiency than to the decrease of feed intake.

TABLE 6

| Experimental group | Body weight gain (g/mouse) | Feed intake (g/mouse) | Feed efficiency (body weight gain/feed intake) |
| --- | --- | --- | --- |
| 1 (0.1% addition) | 4.89 | 61.56 | 0.079 |
| 2 (0.3% addition) | 3.62 | 58.79 | 0.062 |
| 3 (0.5% addition) | 0.84 | 53.58 | 0.016 |
| 4 (lipid free diet) | 4.74 | 64.21 | 0.074 |
| 5 (control) | 5.86 | 61.75 | 0.095 |

The numerical values of the body weight gain and the feed intake show total values throughout the experimental period (4 weeks).

(3) General Conditions and Weight of Organs

No abnormality was observed in the general conditions of each experimental group including appearance, properties of feces, breath and behavior, except for the changes in body weight. As to organ weights, changes correlated with the body weight change were observed in livers, pancreases and kidneys. Absolute weights as well as relative weights of livers were significantly increased in the 0.5% addition group, i.e., 15% and 40%, respectively, and 17% increase of relative weight was observed in the 0.3% addition group. However, no significant difference was observed in the 0.1% addition group. Absolute weights of pancreas decreased in proportion to the amount of the medicament; however, the changes in relative weight was not significant. Kidney weight also decreased in correlation with the amount of the medicament, i.e., 17% decrease of absolute weight and 10% decrease of relative weight in the 0.3% addition group, and 32% decrease of absolute weight and 17% decrease of relative weight in the 0.5% addition group. Decreases of absolute weight of lungs and spleens were observed in the 0.5% addition group; however, their relative weights were not different from those of the control group.

The changes observed in the livers, pancreases, kidneys, and lungs in the groups treated with the medicament were commonly observed in the lipid-free feed group, although the degrees were different. In the lipid-free feed group, absolute weight and relative weight of livers increased by 4% and 6%, respectively, and absolute weight and relative weight of kidneys decreased by 12% and 11%, respectively. These results suggest that the organs of the animals treated with 5-sitosten-3-one were strongly effected in the same manner as those observed in the lipid-free feed group. These changes were not observed when Fischer F344 rats were fed with the feed with 0.5% addition for 4 weeks, and therefore, the changes were considered as unique to CDF1 mice. In addition, in the absence of any histopathological change, the changes were verified as physiological changes caused by the loss of body weight and the alteration of lipid metabolism, or as negligible changes from a viewpoint of toxic influence.

(4) Amount of Intraperitoneal Fat and Serum Lipid Concentration

As shown in Table 7, the amount of intraperitoneal fat was 83% in the 0.1% addition group, 63% in the 0.3% addition group, and 42% in the 0.5% addition group relative to the control group. The lipid-relating values, i.e., triglyceride, total cholesterol, phospholipid, and free fatty acid in plasma decreased depending on the dose of 5-sitosten-3-one. The decrease was particularly remarkable in triglyceride, i.e., decrease down to 26% in the 0.5% addition group as compared to the control group. However, no significant change in HDL-cholesterol was observed. The amount of intraperitoneal fat in the lipid-free feed group decreased to 80% relative to the control group, and serum total cholesterol and phospholipid also significantly decreased. In contrast, triglyceride, HDL-cholesterol, and free fatty acid increased. In the table, asterisk * shows the presence of a significant diffenrece at probability levels (p) of 5% or less in a variance analysis for the groups treated with the medicament and in a t-test for the lipid-free feed group.

TABLE 7

|  | Control | 0.1% | 0.3% | 0.5% | Lipid-free feed |
| --- | --- | --- | --- | --- | --- |
| Intraperitoneal fat (mg) | 1205.0 ± 86.9 | 996.0 ± 53.5 | 760.7 ± 36.9* | 500.6 ± 79.2* | 969.7 ± 48.7* |
| Triglyceride (mg/dl) | 255.2 ± 13.1 | 145.4 ± 8.5* | 78.0 ± 0.9* | 66.8 ± 2.3* | 346.0 ± 9.2* |
| Total cholesterol (mg/dl) | 200.5 ± 10.5 | 164.8 ± 4.0* | 125.5 ± 7.6* | 102.9 ± 6.4* | 186.3 ± 7.0* |
| HDL-cholesterol (mg/dl) | 74.0 ± 6.4 | 68.7 ± 13.6 | 72.5 ± 7.7 | 61.7 ± 4.3 | 91.5 ± 11.9* |
| Phospholipid (mg/dl) | 309.3 ± 12.2 | 237.8 ± 8.9* | 187.0 ± 12.2* | 172.5 ± 8.6* | 285.9 ± 6.1* |
| Free fatty acid (mEq/dl) | 1.44 ± 0.09 | 1.41 ± 0.04* | 1.05 ± 0.06* | 0.87 ± 0.05* | 1.78 ± 0.10* |

Values indicate mean (n = 6) ± standard error.
*Significant difference ($p < 0.05$)

(5) Dose Responding Relationship

Figure 5:
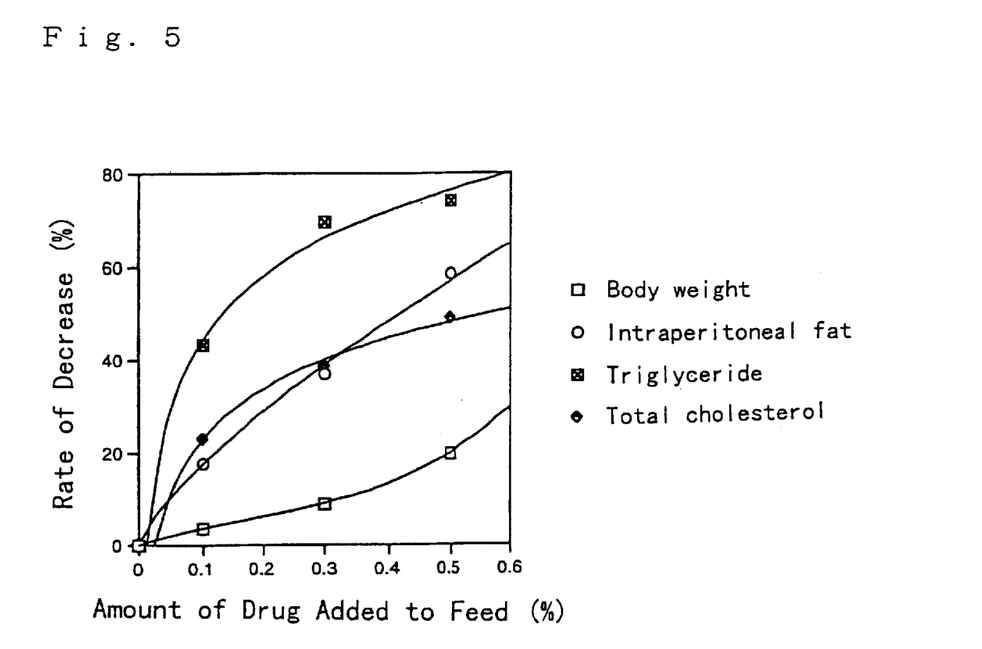
FIG. 5 depicts the correlation of doses of 5-sitosten-3-one added to a feed and body weight, the amount of intraperitoneal fat, the concentrations of serum triglyceride, and total serum cholesterol.

Dose response curves of body weight, body fat, and serum lipid to the dose of 5-sitosten-3-one are shown in FIG. 5. The linear correlation was obtained between the dose of 5-sitosten-3-one and the decrease of intraperitoneal fat of CDF1 mice. The relationships between the dose of 5-sitosten-3-one and plasma triglyceride or total cholesterol was found to be logarithmic decrease, i.e., a curve wherein the magnitude of the decreasing ratio was attenuated dose-dependently. On the other hand, the decreasing ratio of body weight was found to be in a linear relation up to 0.3% addition of the medicament; however, conversely, a logarithmic increase was observed at 0.5% addition. From these results, it is considered that decreasing effects on serum lipids are not satisfactorily expected when the medicament is added in an amount of 0.5% or more. Furthermore, as to the suppression of body weight gain, it was suggested that additional actions other than the primarily desired effects may be induced by an unnecessarily increased amount of the medicament.

(6) Extrapolation to Dose for Human

The amount of 0.3% addition to feeds was assumed as a dose of 5-sitosten-3-one which achieved suffcient effects on the suppressions of body weight gain, body fat, and serum lipid in CDF1 mice. On the basis of the assumption, a dose for humans was calculated. Total feed intake per mouse for three weeks was 58.79 g (Table 6), and the calorie of the consumed experimental feed was 374 kcal/100 g, and accordingly, a caloric intake by one mouse per day was calculated as 10.47 kcal/mouse/day based on the above values. The intake of the medicament by one mouse per day was calculated as 8.4 mg from the amount added to the feed, i.e., 0.3%, and accordingly, the intake of the medicament per 1,000 kcal was calculated as 802 mg/1,000 kcal. From these values and an average daily caloric intake by a Japanese adult (2,500 kcal), a dose for a human was calculated as 2.0 g/man/day.

Example 4

(A) Materials and Methods

5-Campesten-3-one was prepared from campesterol (>97%, Tama Biochemical Industry, Ltd.). 4-Sitosten-3,6-dione was prepared from β-sitosterol (>65%, Tokyo Chemical Industry Co., Ltd.) and obtained as a mixture of 24-ethyl compound and 24-methyl compound (2:1). 5-Stigmasten-3-one was prepared from stigmasterol (>94%, Tokyo Chemical Industry, Co., Ltd.). As experimental animals, six CDF1 male mice (5-week old, Charles River Japan Inc.) were used in each experimental group. Modified AIN (Oriental Yeast Co.) was used as basic feed and mixed with 0.5% of each test compound to prepare test feeds. The animals were allowed to feed with the test food ad libitum for 14 days. Measurements of body weights and observations of general conditions of the animals were carried out twice a week, and the animals were subjected to autopsy and their bloods were collected. Serum lipid analysis was conducted by using a clinical test kit based on the enzymatic method (Wako Pure Chemicals Industries Co., Ltd.). Significances of the resulting values were examined by the one-way analysis of variance with pairwise comparison (ANOVA) according to the Bonferroni method. Other conditions were the same as those described in Example 1.

(B) Test Results (1) Changes in Body Weight

Figure 6:
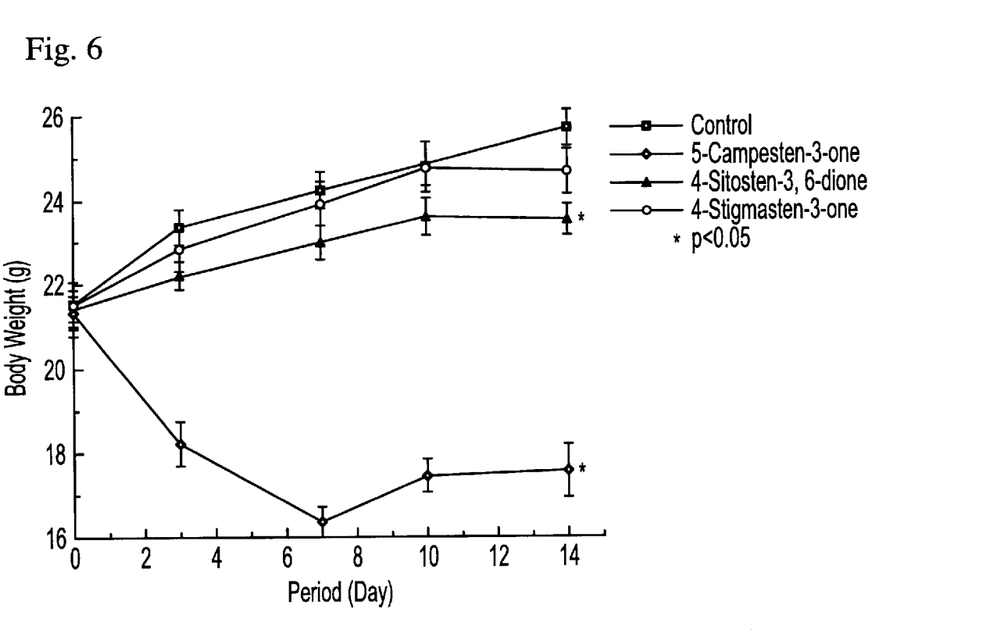
FIG. 6 depicts inhibitory effect of 5-campesten-3-one, 4-sitosten-3,6-dione, and 5-stigmasten-3-one on the weight gain of mice. The values in the figure are indicated as mean±standard error and asterisks * shows the presence of a significant decrease from the non-treated control mice at a probability (p) level of 5% or less in the analysis of variance with pairwise comparison (ANOVA).

The changes in body weight of the test animals are shown in FIG. 6. Significant inhibitory effects on the increase of body weight were observed in the mice administered with 5-campesten-3-one and 4-sitosten-3,6-dione. In particular, 5-campesten-3-one remarkably suppressed the increase in body weight. In the figure, asterisk * indicates the presence of a significant decrease from the non-treated mice at probability (p) level of 5% or less in the ANOVA.

(2) Changes in the Amount of Body Fat

Significant decrease of body fat were observed in the mice fed with the feed supplemented with 5-campesten-3-one or 4-sitosten-3,6-dione (Table 8, about 90% and 40%, respectively). In the table, asterisk * indicates the presence of a significant decrease from the non-treated mice at probability (p) level of 5% or less in the ANOVA.

(3) Changes in Serum Lipid Concentration

Effects of the tested compounds on serum lipid concentration are shown in Table 8. Serum triglyceride concentration was significantly decreased by the administration of 5-campesten-3-one, 4-sitosten-3,6-dione, and 5-stigmasten-3-one (about 45%, 66%, and 68% decrease, respectively). Serum total cholesterol concentration was also significantly decreased by the administration of 5-campesten-3-one, 4-sitosten-3,6-dione, and 5-stigmasten-3-one (about 34%, 18%, and 49%, respectively). In the table, asterisk * indicates the presence of a significant decrease from the non-treated mice at probability (p) level of 5% or less in the ANOVA according to the Bonferroni method.

(4) General Conditions and Autopsical Finding

No toxicological abnormality was observed in general conditions and the autopsical finding of the mice.

TABLE 8

|  | Control | 5-Campesten-3-one | 4-Sitosten-3,6-diono | 5-Stigmasten-3-one |
|---|---|---|---|---|
| Intraperitoneal fat (mg) | 826.4 ± 84.9 | 86.4 ± 19.9* | 472.7 ± 37.7* | 745.7 ± 46.7 |
| Triglyceride (mg/dl) | 253.4 ± 18.1 | 138.9 ± 18.7* | 85.8 ± 9.2* | 82.0 ± 6.7* |
| Total cholesterol (mg/dl) | 191.2 ± 7.5 | 125.8 ± 4.0* | 156.3 ± 6.4* | 97.9 ± 3.4* |

Values indicate mean (n = 6) ± standard error.
*Significant difference (p < 0.05)

What is claimed is:

1. A method for therapeutic or prophylactic treatment of obesity, comprising administering to a mammal in need thereof a therapeutically or prophylactically effective amount of a medicament comprising at least one 24-alkylcholest-5-en-3-one and a food product.

2. A method for therapeutic or prophylactic treatment of obesity, comprising administering to a mammal in need thereof a therapeutically or prophylactically effective amount of at least one 24-alkylcholest-5-en-3-one.

3. The method according to claim 2 wherein the at least one 24-alkylcholest-5-en-3-one comprises at least one of 5-sitosten-3-one and 5-campesten-3-one.

4. The method according to claim 2 wherein the at least one 24-alkylcholest-5-en-3-one comprises 5-campesten-3-one.

5. The method according to claim 2 wherein the method is the prophylactic treatment of obesity.

6. The method according to claim 2 wherein the method is the therapeutic treatment of obesity.

7. The method according to claim 2 wherein the at least one 24-alkylcholest-5-en-3-one is contained in a health food.

8. The method according to claim 2 wherein the at least one 24-alkylcholest-5-en-3-one is contained in a health beverage.

9. The method according to claim 2 wherein the at least one 24-alkylcholest-5-en-3-one is contained in animal feed.

10. The method according to claim 2 wherein the at least one 24-alkylcholest-5-en-3-one is contained in pet food.

* * * * *